(12) United States Patent
Byun et al.

(10) Patent No.: US 7,638,158 B2
(45) Date of Patent: Dec. 29, 2009

(54) DRUG RELEASE FROM ANTITHROMBOGENIC MULTI-LAYER COATED STENT

(75) Inventors: Youngro Byun, Seoul (KR); Jung Han Yoon, Seoul (KR)

(73) Assignee: Mediplex Corporation, Korea, Seoul (KR)

( * ) Notice: Subject to any disclaimer, the term of this patent is extended or adjusted under 35 U.S.C. 154(b) by 1026 days.

(21) Appl. No.: 10/797,629

(22) Filed: Mar. 9, 2004

(65) Prior Publication Data

US 2004/0254638 A1 Dec. 16, 2004

Related U.S. Application Data

(62) Division of application No. 10/262,432, filed on Sep. 30, 2002, now Pat. No. 6,702,850.

(51) Int. Cl.
*A61L 33/10* (2006.01)
*A61L 33/12* (2006.01)
*A61L 2/06* (2006.01)

(52) U.S. Cl. .................. 427/2.24; 427/2.1; 427/2.25; 623/1.42; 623/1.43; 623/1.44; 623/1.47

(58) Field of Classification Search ............ 427/2.1, 427/2.24, 2.25
See application file for complete search history.

(56) References Cited

U.S. PATENT DOCUMENTS

| | | |
|---|---|---|
| 4,239,754 A | 12/1980 | Sache et al. |
| 4,857,602 A | 8/1989 | Casey et al. |
| 5,536,508 A | 7/1996 | Canal et al. |
| 5,626,869 A | 5/1997 | Nyqvist et al. |

(Continued)

FOREIGN PATENT DOCUMENTS

WO   WO 00/13719   3/2000

(Continued)

OTHER PUBLICATIONS

Van Delden et al. The effect of protein adsorption on the anticoagulant activity of surface immobilized heparin, 1996, J. Biomaterial Science Polymer Edn. vol. 7, No. 8 pp. 727-740.*

(Continued)

*Primary Examiner*—Timothy H Meeks
*Assistant Examiner*—Cachet I Sellman
(74) *Attorney, Agent, or Firm*—Clayton, Howarth & Cannon, P.C.

(57) ABSTRACT

A stent having a multi-layered coating adhered to its surface which can prevent restenosis and thrombosis at the implant site. The stent coating is comprised of two layers. The first layer is a polymeric coating with one or more biologically active agent(s) dispersed therein. The second layer is comprised of a hydrophobic heparinized polymer that inhibits blood coagulation and provides a hydrophilic surface for reducing the friction between stent and lesion site. In preferred embodiments of the invention, the multi-layered stent is effective in deterring restenosis and thrombosis at the implant site. In these same preferred embodiments, the multi-layered stent is capable of reducing the burst release of the biologically active agents from the first layer and sustaining a release of an effective amount of these agents for a relatively extended period of time. Methods of applying the multi-layered coating to the stent surface are also part of this invention.

19 Claims, 11 Drawing Sheets

U.S. PATENT DOCUMENTS

| | | | |
|---|---|---|---|
| 5,700,486 | A | 12/1997 | Canal et al. |
| 5,744,155 | A | 4/1998 | Friedman et al. |
| 5,782,908 | A | 7/1998 | Cahalan et al. |
| 5,820,881 | A | 10/1998 | Milstein |
| 5,833,651 | A * | 11/1998 | Donovan et al. ............. 604/509 |
| 5,837,313 | A | 11/1998 | Ding et al. |
| 5,840,387 | A | 11/1998 | Berlowitz-Tarrant et al. |
| 5,855,618 | A | 1/1999 | Patnaik et al. |
| 5,955,588 | A * | 9/1999 | Tsang et al. ................... 536/21 |
| 5,993,846 | A | 11/1999 | Friedman et al. |
| 5,993,972 | A | 11/1999 | Reich et al. |
| 6,153,252 | A | 11/2000 | Hossainy et al. |
| 6,190,591 | B1 | 2/2001 | van Lengerich |
| 6,245,753 | B1 * | 6/2001 | Byun et al. .................... 514/56 |
| 6,248,363 | B1 | 6/2001 | Patel et al. |
| 6,251,142 | B1 * | 6/2001 | Bernacca et al. ......... 623/23.57 |
| 6,251,428 | B1 | 6/2001 | Yoo |
| 6,258,121 | B1 * | 7/2001 | Yang et al. ................. 623/1.46 |
| 6,306,144 | B1 | 10/2001 | Sydney et al. |
| 6,355,058 | B1 | 3/2002 | Pacetti et al. |
| 6,361,819 | B1 | 3/2002 | Tedeschi et al. |
| 6,376,242 | B1 | 4/2002 | Hanson |
| 6,395,253 | B2 | 5/2002 | Levy et al. |
| 6,399,144 | B2 | 6/2002 | Dinh et al. |
| 7,129,224 | B1 * | 10/2006 | Byun et al. .................... 514/56 |
| 2002/0091433 | A1 * | 7/2002 | Ding et al. .................... 623/1.2 |

FOREIGN PATENT DOCUMENTS

| | | |
|---|---|---|
| WO | WO 02/34312 | 5/2002 |

OTHER PUBLICATIONS

R. Altman et al. Oral Anticoagulant Treatment with and without Aspirin, *Thrombosis and Haemostasis*, 74, 506-510 (1995).

D. Brayden et al. Heparin Absorption Across the Intestine: Effects of Sodium N-[-(2-Hydroxybenzoyl)Amino]Caprylate in Rate In Situ Intestinal Instillations and in Caco-2 Monolayers, *Pharmaceutical Research*, 14, 1772-1779 (1997).

F. Diancourt et al. Chemical Modifications of Heparin. II. Hydrophobization of Partially N-Desulfated Heparin, *Journal of Bioactive and Compatible Polymers*, 11, 203-218 (1996).

R.D. Hull, MD et al. Hirudin versus heparin and low-molecular-weight heparin: And the winner is . . . *J Lab Clin Med*, 132, 171-174, (1998).

P. Klement et al. Hirudin causes more bleeding than heparin in a rabbit ear bleeding model, *J Lab Clin Med* 132, 181-185 (1998).

B.G. Koefoed et al. Effect of Fixed Minidose Warfarin, Conventional Dose Warfarin and Aspirin on INR and Prothrombin Fragment 1 + 2 in Patients with Atrial Fibrillation, *Thrombosis and Haemostasis*, 77, 845-848 (1997).

Y-k Lee, et al. Preparation of Slightly Hydrophobic Heparin Derivatives which Can Be Used for Solvent Casting in Polymeric Formulation, *Thrombosis Research* 92, 149-156 (1998).

Y-k Lee et al. Oral Delivery of New Heparin Derivatives in Rats, *Pharmaceutical Research*, 17, 1-5 (2000).

A. Leone-Bay et al. 4-[4[(2-Hydroxybenzoyl)amino]phenyl]butyric Acid as a Novel Oral Delivery Agent for Recombinant Human Growth Hormone, *J. Med. Chem.*, 39, 2571-2578 (1996).

A. Leone-Bay et al. The evolution of an oral heparin dosing solution, *Drugs of the Future*, 22, 885-891 (1997).

A. Leone-Bay et al. Oral Delivery of Sodium Cromolyn: Preliminary Studies In Vivo and In Vitro, *Pharmaceutical Research*, 13, 222-226 (1996).

A. Leone-Bay et al. N-Acylated α-Amino Acids as Novel Oral Delivery Agents for Proteins, *J. Med. Chem.*, 38, 4263-4269 (1995).

A. Leone-Bay et al. Acylated non-α-amino acids as novel agents for the oral delivery of heparin sodium, USP, *Journal of Controlled Release*, 50, 41-49 (1998).

A. Leone-Bay et al. Synthesis and Evaluation of Compounds That Facilitate the Gastrointestinal Absorption of Heparin, *J. Med. Chem.*, 41, 1163-1171(1998).

A. Leone-Bay et al. Microsphere Formation in a Series of Derivatized α-Amino Acids: Properties, Molecular Modeling, and Oral Delivery of Salmon Calcitonin, *J. Med. Chem.*, 38, 4257-4262 (1995).

S.J. Milstein et al. Partially unfolded proteins efficiently penetrate cell membranes—implications for oral drug delivery, *Journal of Controlled Release*, 53, 259-267 (1998).

G. E. Raskob, Msc. Low molecular weight heparin, heparin, and warfarin, *Current Opinion in Hematology* 2, 372-379 (1995).

G.J. Russell-Jones, Carrier-Mediated Transport, Oral Drug Delivery, in *Encyclopedia of Controlled Drug Delivery*, 1, 173-183 (E. Mathiowitz, ed. 1999).

P. W. Swaan et al. Enhanced Transepithelial Transport of Peptides by Conjugation to Cholic Acid, *Bioconjugate Chem*. 8, 520-525 (1997).

L. Wallentin, Unstable coronary artery disease—need for long term antithrombotic treatment Aspirin alone is not sufficient, I would associate an anticoagulant, *Cardiovascular Research*, 33, 292-294 (1997).

E. Windsor et al. Gastro-Intestinal Absorption of Heparin and Synthetic Heparinoids, *Nature*, 190, 263-264 (1961).

* cited by examiner

A    B    C

DRUG RELEASE FROM ANTITHROMBOGENIC MULTI-LAYER COATED STENT

CROSS-REFERENCE TO RELATED APPLICATIONS

This application is a division of U.S. application Ser. No. 10/262,432, filed Sep. 30, 2002, now U.S. Pat. No. 6,702,850, which is hereby incorporated in its entirety.

STATEMENT REGARDING FEDERALLY SPONSORED RESEARCH OR DEVELOPMENT

Not applicable.

BACKGROUND OF THE INVENTION

This invention relates to coated stents for carrying biologically active agents to provide localized treatment at the implant site and methods of applying stent coatings. In particular, this invention relates to antithrombogenic and antirestenotic stents having a multi-layered coating, wherein the first or inner layer is formed from a polymer and one or more biologically active agents, and a second or outer layer is formed from an antithrombogenic heparinized polymer. This invention also relates to methods of applying a multi-layer coating over the surface of a stent and methods of using such a coated stent.

Atherogenic arterial narrowing and thrombosis are two potentially fatal, related conditions that have been identified as leading killers by various health organizations in the United States and throughout the world. Stenosis refers to the narrowing or constriction of a vessel, which is usually due to the buildup of fat, cholesterol, and other substances over time. In severe cases, stenosis can completely clog a vessel. Thrombosis is the formation or presence of a blood clot inside a blood vessel or cavity of the heart. The clot is usually formed by an aggregation of blood factors, primarily platelets and fibrin, with entrapment of cellular elements. Thrombosis, like stenosis, frequently causes vascular obstruction at the point of its formation.

One approach to clearing an artery that has been constricted or clogged due to stenosis is percutaneous transluminal coronary angioplasty (PTCA) or balloon coronary angioplasty. In this procedure, a balloon catheter is inserted and expanded in the constricted portion of the vessel for clearing the blockage. About one-third of patients who undergo PTCA suffer from restenosis, the renarrowing of the widened segment, within about six months of the procedure. Restenosed arteries may have to undergo another angioplasty.

Restenosis can be inhibited by a common procedure that consists of inserting a stent into the effected region of the artery instead of, or along with, angioplasty. A stent is a tube made of metal or plastic, which can have either solid walls or mesh walls. Most stents in use are metallic and are either self-expanding or balloon-expandable. The decision to undergo a stent insertion procedure depends on certain features of the arterial stenosis. These include the size of the artery and the location of the stenosis. The function of the stent is to buttress the artery that has recently been widened using angioplasty, or, if no angioplasty was used, the stent is used to prevent elastic recoil of the artery. Stents are typically implanted via a catheter. In the case of a balloon-expandable stent, the stent is collapsed to a small diameter and slid over a balloon catheter. The catheter is then maneuvered through the patient's vasculature to the site of the lesion or the area that was recently widened. Once in position, the stent is expanded and locked in place. The stent stays in the artery permanently, holds it open, improves blood flow through the artery, and relieves symptoms (usually chest pain).

Stents are not 100% effective in preventing restenosis at the implant site. Restenosis can occur over the length of the stent and/or past the ends of the stent. Physicians have recently employed new types of stents that are coated with a thin polymer film loaded with a drug that inhibits smooth cell proliferation. The coating is applied to the stent prior to insertion into the artery using methods well known in the art, such as a solvent evaporation technique. The solvent evaporation technique entails mixing the polymer and drug in a solvent. The solution comprising polymer, drug, and solvent can then be applied to the surface of the stent by either dipping or spraying. The stent is then subjected to a drying process, during which the solvent is evaporated, and the polymeric material, with the drug dispersed therein, forms a thin film layer on the stent.

The release mechanism of the drug from the polymeric materials depends on the nature of the polymeric material and the drug to be incorporated. The drug diffuses through the polymer to the polymer-fluid interface and then into the fluid. Release can also occur through degradation of the polymeric material. The degradation of the polymeric material occurs through hydrolysis, which erodes the polymer into the fluid and hence releases the drug into the fluid as well.

An important consideration in using coated stents is the release rate of the drug from the coating. It is desirable that an effective therapeutic amount of the drug be released from the stent for the longest period of time possible. Burst release, a high release rate immediately following implantation, is undesirable and a persistent problem. While typically not harmful to the patient, a burst release "wastes" the limited supply of the drug by releasing several times the effective amount required and shortens the duration of the release period. Several techniques have been developed in an attempt to reduce burst release. For example, U.S. Pat. No. 6,258,121 B1 to Yang et al. discloses a method of altering the release rate by blending two polymers with differing release rates and incorporating them into a single layer.

Heparin, generally derived from swine intestine, is a substance that is well known for its anticoagulation ability. It is known in the art to apply a thin polymer coating loaded with heparin onto the surface of a stent using the solvent evaporation technique. For example, U.S. Pat. No. 5,837,313 to Ding et al. describes a method of preparing a heparin coating composition.

In view of the foregoing, it will be appreciated that the development of a stent having a multi-layered coating, where one layer comprises a thin film of polymeric material with a biologically active agent dispersed therein, and a second layer is disposed over the first layer where the second layer comprises a hydrophobic heparinized polymer, would be a significant advance in the art. It will also be appreciated that the current invention inhibits both restenosis and thrombosis, and can be effective in delivering a wide range of other therapeutic agents to the implant site over a relatively extended period of time.

BRIEF SUMMARY OF THE INVENTION

The present invention provides a stent having a multi-layered coating comprising at least two layers disposed one on top of the other for inhibiting restenosis and thrombosis through the delivery of biologically active agents over a sustained period of time. The first layer comprises a polymeric material with a biologically active agent dispersed therein, and the second layer comprises a hydrophobic heparinized polymer having effective anticoagulation characteristics. This invention also provides several methods for applying multiple inner layers of a coating onto a stent, with the hydrophobic heparinized polymer being applied as the outer and final layer of the coating.

The first or sub-layer is prepared by mixing a polymeric material and a biologically active agent with a solvent, thereby forming a homogeneous solution. The polymeric material can be selected from a wide range of synthetic materials, but in one illustrative embodiment, polyacrylic acid is used. The biologically active agent is selected depending on the desired therapeutic results. For example, an anticancer drug and/or antiinflammatory drug can be used. By way of further example, if an inhibitor of smooth cell proliferation is desired, echinomycin or paclitaxel can be used. Once prepared, the solution can be applied to the stent through a dipping or spraying process. During drying, the solvent evaporates, and a thin layer of the polymeric material loaded with the biologically active agent is left coated over the stent. It should be noted that the current invention is not limited to just one inner layer or biologically active agent per layer. It is within the scope of this invention to add one or more distinct biologically active agents to each layer and/or have more than one inner layer loaded with a biologically active agent.

The second or outer layer is an antithrombogenic heparinized polymer applied to the stent over the inner layer using, for example, a dipping process. The antithrombogenic heparinized polymer coating is prepared by bonding multifunctional macromolecules, such as polyacrylic acid, and hydrophobic materials, such as octadecylamine, with heparin. In one illustrative embodiment of the invention, the hydrophobic material has more than one reactive functional group and under 100 mg/ml water solubility after being combined with a macromolecule. The stent is then dipped in the hydrophobic heparinized polymer, which has been mixed with a solvent. After drying, the solvent evaporates and the hydrophobic heparinized polymer forms a thin film over the first layer.

The coated stent is inserted into the afflicted vessel, such as a coronary artery, using an appropriate procedure that depends on the stent style. Once in place, the stent structure will hold the vessel open. The biologically active agent will be released from the first layer, thereby providing the desired therapeutic result, such as inhibiting smooth cell proliferation. The antithrombogenic heparinized polymer prevents blood coagulation around the stent, thus inhibiting thrombosis and subacute stent thrombosis. In addition, the antithrombogenic heparinized polymer layer reduces or prevents the burst release of the biologically active agent from the first layer, thereby allowing the release to occur over a relatively extended period of time.

Accordingly, it is an advantage of this invention to provide a stent capable of inhibiting restenosis and thrombosis at the implantation site.

It is also an advantage of the invention to provide a stent having a multi-layered coating for delivering biologically active agents that inhibit smooth cell proliferation and blood clots.

It is still another advantage of the invention to provide a stent having a multi-layered coating having an outer layer comprising an antithrombogenic heparinized polymer.

It is still another advantage of the invention to provide a stent having a multi-layered coating for delivering a wide range of therapeutic agents over a relatively extended period of time and mitigating the burst release of the biologically active agent from the inner layer or layers.

It is yet another advantage of the invention to provide a method for applying a multi-layered coating to the surface of a stent.

DETAILED DESCRIPTION

Figure 1:
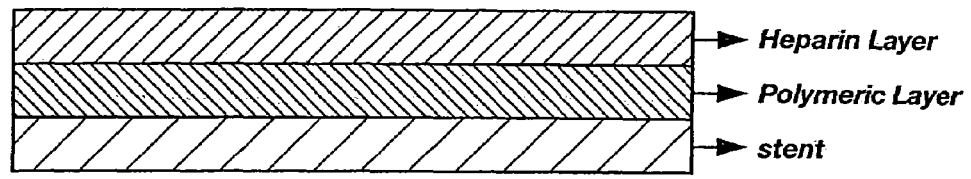
FIG. 1 is a cross-sectional representation of a fragmentary portion of a stent showing the first and second layers of the stent coating.

Before the present stent having a multilayered coat and methods for using and preparing a stent having a multi-layered coating are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

The publications and other reference materials referred to herein to describe the background of the invention and to provide additional detail regarding its practice are hereby incorporated by reference. The references discussed herein are provided solely for their disclosure prior to the filing date of the present application. Nothing herein is to be construed as an admission that the inventors are not entitled to antedate such disclosure by virtue of prior invention.

It must be noted that, as used in this specification and the appended claims, the singular forms "a," "an," and "the" include plural referents unless the context clearly dictates otherwise. Thus, for example, reference to "a biologically active agent" includes a mixture of two or more of such agents, reference to "an inhibitor" includes reference to one or more of such inhibitors, and reference to "the solvent" includes reference to a mixture of two or more solvents.

In describing and claiming the present invention, the following terminology will be used in accordance with the definitions set out below.

As used herein, "stent" means a tube of metal or plastic that is inserted into a vessel or passage to keep the lumen open and prevent closure due to a stricture or external compression.

As used herein, "biologically active agent" means a drug or other substance that has therapeutic value to a living organism including without limitation antithrombotics, anticoagulants, antiplatelet agents, thrombolytics, antiproliferatives, anti-inflammatories, agents that inhibit restenosis, smooth muscle cell inhibitors, antibiotics, and the like, and mixtures thereof.

Illustrative anticancer drugs include acivicin, aclarubicin, acodazole, acronycine, adozelesin, alanosine, aldesleukin, allopurinol sodium, altretamine, aminoglutethimide, amonafide, ampligen, amsacrine, androgens, anguidine, aphidicolin glycinate, asaley, asparaginase, 5-azacitidine, azathioprine, *Bacillus* calmette-guerin (BCG), Baker's Antifol (soluble), beta-2'-deoxythioguanosine, bisantrene hcl, bleomycin sulfate, busulfan, buthionine sulfoximine, BWA 773U82, BW 502U83.HCl, BW 7U85 mesylate, ceracemide, carbetimer, carboplatin, carmustine, chlorambucil, chloroquinoxalinesulfonamide, chlorozotocin, chromomycin A3, cisplatin, cladribine, corticosteroids, *Corynebacterium* parvum, CPT-11, crisnatol, cyclocytidine, cyclophosphamide, cytarabine, cytembena, dabis maleate, dacarbazine, dactinomycin, daunorubicin HCl, deazauridine, dexrazoxane, dianhydrogalactitol, diaziquone, dibromodulcitol, didemnin B, diethyldithiocarbamate, diglycoaldehyde, dihydro-5-azacytidine, doxorubicin, echinomycin, edatrexate, edelfosine, eflornithine, Elliott's solution, elsamitrucin, epirubicin, esorubicin, estramustine phosphate, estrogens, etanidazole, ethiofos, etoposide, fadrazole, fazarabine, fenretinide, filgrastim, finasteride, flavone acetic acid, floxuridine, fludarabine phosphate, 5-fluorouracil, Fluosol®, flutamide, gallium nitrate, gemcitabine, goserelin acetate, hepsulfam, hexamethylene bisacetamide, homoharringtonine, hydrazine sulfate, 4-hydroxyandrostenedione, hydrozyurea, idarubicin HCl, ifosfamide, interferon alfa, interferon beta, interferon gamma, interleukin-1 alpha and beta, interleukin-3, interleukin-4, interleukin-6, 4-ipomeanol, iproplatin, isotretinoin, leucovorin calcium, leuprolide acetate, levamisole, liposomal daunorubicin, liposome encapsulated doxorubicin, lomustine, lonidamine, maytansine, mechlorethamine hydrochloride, melphalan, menogaril, merbarone, 6-mercaptopurine, mesna, methanol extraction residue of *Bacillus* calmette-guerin, methotrexate, N-methylformamide, mifepristone, mitoguazone, mitomycin-C, mitotane, mitoxantrone hydrochloride, monocyte/macrophage colony-stimulating factor, nabilone, nafoxidine, neocarzinostatin, octreotide acetate, ormaplatin, oxaliplatin, paclitaxel, pala, pentostatin, piperazinedione, pipobroman, pirarubicin, piritrexim, piroxantrone hydrochloride, PIXY-321, plicamycin, porfimer sodium, prednimustine, procarbazine, progestins, pyrazofurin, razoxane, sargramostim, semustine, spirogermanium, spiromustine, streptonigrin, streptozocin, sulofenur, suramin sodium, tamoxifen, taxotere, tegafur, teniposide, terephthalamidine, teroxirone, thioguanine, thiotepa, thymidine injection, tiazofurin, topotecan, toremifene, tretinoin, trifluoperazine hydrochloride, trifluridine, trimetrexate, tumor necrosis factor, uracil mustard, vinblastine sulfate, vincristine sulfate, vindesine, vinorelbine, vinzolidine, Yoshi 864, zorubicin, and mixtures thereof.

Illustrative antiinflammatory drugs include classic non-steroidal anti-inflammatory drugs (NSAIDS), such as aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone (relafen), acetaminophen (Tylenol®), and mixtures thereof; COX-2 inhibitors, such as nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof; glucocorticoids, such as hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, and mixtures thereof; and mixtures thereof.

As used herein, "polymer" means a macromolecule made of repeating monomer units or protomers.

As used herein, "macromolecule" means synthetic macromolecules, proteins, biopolymers and other molecules with a molecular weight typically greater than 1000.

As used herein, "antithrombogenic heparinized polymer," "hydrophobic heparinized polymer," and similar terms mean hydrophobic multicomponent heparin conjugates as described International Patent Application No. PCT/KR00/01255 (WO 02/34312 A1), co-owned with the present invention, which is incorporated herein by reference in its entirety. These hydrophobic heparinized polymers comprise a conjugate comprising heparin, a macromolecular component, and a hydrophobic component.

As used herein, "effective amount" means an amount of pharmacologically active agent that is nontoxic but sufficient to provide the desired local or systemic effect and performance at a reasonable benefit/risk ratio attending any medical treatment.

The present invention relates to an antithrombogenic stent having a multi-layered coating. In an illustrative embodiment, the first layer comprises a polymeric film loaded with a biologically active agent that prevents smooth cell proliferation, such as echinomycin. Illustrative polymers that can be used for making the polymeric film include polyurethanes, polyethylene terephthalate (PET), PLLA-poly-glycolic acid (PGA) copolymer (PLGA), polycaprolactone (PCL), poly-(hydroxybutyrate/hydroxyvalerate) copolymer (PHBV), poly(vinylpyrrolidone) (PVP), polytetrafluoroethylene (PTFE, Teflon™), poly(2-hydroxyethylmethacrylate) (poly- HEMA), poly(etherurethane urea), silicones, acrylics, epoxides, polyesters, urethanes, parlenes, polyphosphazene polymers, fluoropolymers, polyamides, polyolefins, and mixtures thereof. The second layer comprises a hydrophobic heparinized polymer with strong anticoagulation properties. The second layer of the hydrophobic heparinized polymer also has the effect of preventing a burst release of the biologically active agent dispersed in the first layer—resulting in a relatively longer release period of the biologically active agent. It should also be understood that the first layer can contain more than one biologically active agent.

The style and composition of the stent may comprise any biocompatible material having the ability to support a diseased vessel. In general, it is preferred to use a metal stent, such as those manufactured from stainless steel, gold, titanium or the like, but plastic or other appropriate materials may be used. In one preferred embodiment, the stent is a Palmz-Schatz stent manufactured by Cordis Corp. (Miami, Fla.). The stent may be self expanding or balloon expanding. It is preferred that the coating substantially cover the entire stent surface, but it is within the scope of this invention to have the coating cover only a portion of the stent. It is also to be understood that any substrate, medical device, or part thereof having contact with organic fluid, or the like, may also be coated.

The application of the first layer is accomplished through a solvent evaporation process or some other known method. The solvent evaporation process entails combining the polymeric material and the biologically active agent with a solvent, such as tetrahydrofuran (THF), which are then mixed by stirring to form a mixture. An illustrative polymeric material of the first layer comprises polyurethane and an illustrative biologically active agent comprises echinomycin. The mixture is then applied to the surface of the stent by either: (1) spraying the solution onto the stent; or (2) dipping the stent into the solution. After the mixture has been applied, the stent is subjected to a drying process, during which, the solvent evaporates and the polymeric material and biologically active agent form a thin film on the stent. In another illustrative embodiment, more than one biologically active agent can be added to the first layer.

The second layer of the stent coating comprises an antithrombogenic heparinized polymer. Antithrombogenic heparinized polymers are soluble only in organic solvents and are insoluble in water. Antithrombogenic heparin polymers are produced by binding heparin to macromolecules and hydrophobic materials.

Illustrative macromolecules include synthetic macromolecules, proteins, biopolymers, and mixtures thereof. Illustrative synthetic macromolecules include polydienes, polyalkenes, polyacetylenes, polyacrylic acid and its derivatives, poly α-substituted acrylic acid and its derivatives, polyvinyl ethers, polyvinylalcohol, polyvinyl halides, polystyrene and its derivatives, polyoxides, polyethers, polyesters, polycarbonates, polyamides, polyamino acids, polyureas, polyurethanes, polyimines, polysulfides, polyphosphates, polysiloxanes, polysilsesquioxanes, polyheterocyclics, cellulose and its derivatives, and polysaccharides and their copolymers or derivatives. Illustrative proteins that can be used according to the present invention include protamine, polylysine, polyaspartic acid, polyglutamic acid, and derivatives and copolymers thereof. Illustrative biopolymers that can be used according to the present invention include polysaccharides, gelatin, collagen, alginate, hyaluronic acid, alginic acid, carrageenan, chondroitin, pectin, chitosan, and derivatives and copolymers thereof. In an illustrative embodiment, the antithrombogenic heparin polymer is prepared by the following steps. First, the macromolecules are activated by using N,N-dicyclohexylcarbodiimide hydrochloride (DDC) or 4-p-azidosalicylamido-butylamine (ASBA). Second, binding heparin, recombinant heparin, heparin derivatives or heparin analogues (having a preferred weight of 1,000-1,000,000 daltons) to the macromolecules. While covalent bonds can formed between the heparin and macromolecules by using the hydroxyl group, amine group, thiol group or azide group, it is preferred to use the amine group. Lastly, the hydrophobic materials are bound with the functional groups of the macromolecule which has already been combined with heparin. While it is understood that any hydrophobic material that has a functional group can be used, it is preferred to use octadecylamine, alkanoic amine, bile acids, sterols, or alkanoic acids.

Once the hydrophobic heparinized polymer has been prepared, the second layer is applied directly over the first layer using the solvent evaporation method or other appropriate method. The hydrophobic heparinized polymer is readied for application by combining it with a solvent, such as cyclohexane, thereby forming an aqueous solution having the hydrophobic heparinized polymer suspended therein. The antithrombogenic heparinized polymer and solvent solution is then applied to the stent using a dipping process. The solvent is evaporated from the stent during a drying process; leaving a thin film of the hydrophobic heparinized polymer over the first layer.

The antithrombogenic heparinized polymer layer inhibits coagulation at the implant site. In addition, the second layer inhibits or prevents a burst release of the biologically active agent from the first layer. The second layer also serves to extend the release period of the biologically active agent from the first layer, thereby lengthening the treatment time.

EXAMPLE 1

Preparation of a Multi-Layer Coating on a Stent by a Dip-Coating Method. A coating solution for the first layer was prepared by combining and agitating a polymer, biologically active agent and THF, until thoroughly mixed. The polymer selected was polyurethane and had a concentration of 3 wt %. The biologically active agent was paclitaxel and had a concentration range of 0 to 20 wt %. Prior to applying the first layer, the stent's surface was prepared and cleaned by washing it with methanol and drying it in a vacuum drier for approximately 30 minutes. Once dry, the cleaned stent was fully immersed into the first coating solution and dried at room temperature for approximately 5 hours in a beaker saturated with THF. This dipping/drying process was repeated 5 times. After the fifth repetition, the stent was dried at room temperature for about 1 hour in a vacuum drier.

The second layer coating solution was prepared by mixing the hydrophobic heparinized polymer, 0.1 to 20 wt %, in cyclohexane. The stent was then dipped into the heparinized polymer solution and dried at room temperature for 1 hour, followed by drying in a vacuum drier at room temperature for 6 hours. The two-layer coating as applied on the surface of a stent is illustrated in FIG. 1.

EXAMPLE 2

Preparation of a Multi-Layered Coating on a Stent by a Spray-Coating Method. A coating solution for the first layer and stent were prepared as described in Example 1. The prepared first-layer solution was then sprayed on the cleaned stent for approximately 10 minutes and dried at room temperature. This spraying/drying process was repeated 10 times, after which the stent was dried in a vacuum drier for approximately 1 hour. The second coating layer, the hydrophobic heparinized polymer solution, was applied as described in Example 1. The two-layer coating as applied on the surface of a stent is illustrated in FIG. 1.

EXAMPLE 3

Preparation of a Multi-Layer Coated Stent Loaded with Two Biologically Active Agents. The first layer coating solution was prepared by combining and agitating polyurethane, paclitaxel, dexamethasone in THF until thoroughly mixed. The loading amounts of the biologically active agents were 0 to 20 wt %, respectively. The stent was cleaned as described in Example 1. The prepared solution was sprayed on the stent for approximately 10 minutes and dried at room temperature. After the spray process was repeated for 10 times, the stent was dried under vacuum for 1 hour. The second layer, a hydrophobic heparinized polymer solution, was applied as described in Example 1.

EXAMPLE 4

Figure 2A:
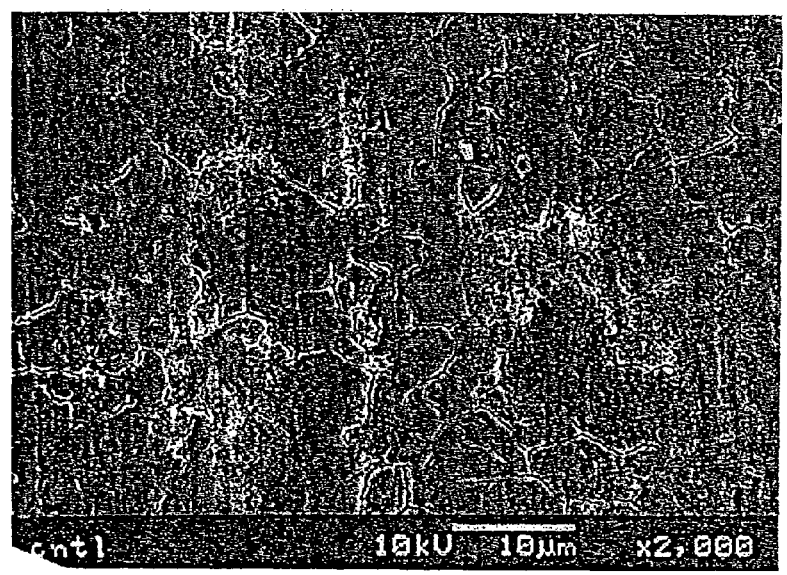
FIG. 2(a) is a scanning electron microscope (SEM) image from a rough surface of a bare stent, magnified 2,000 times.
Figure 2B:
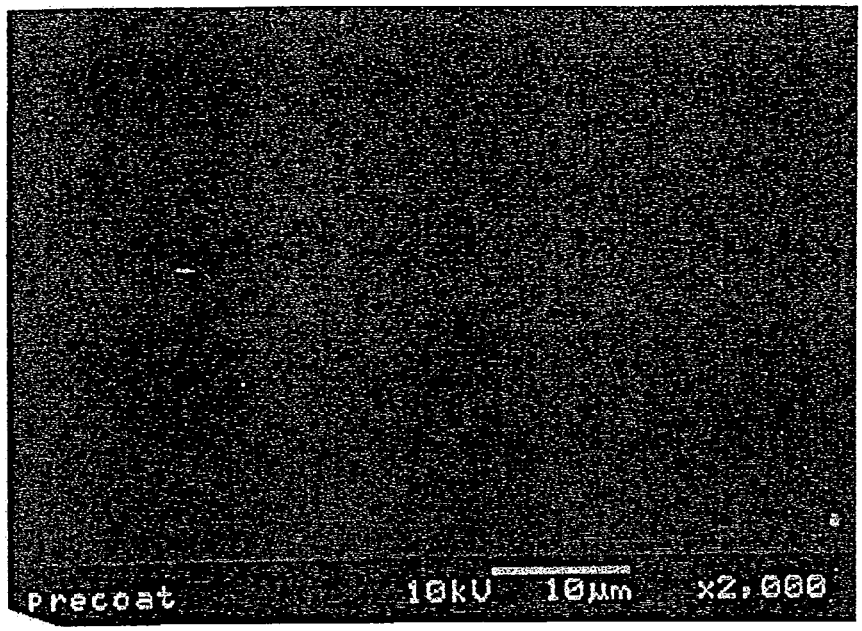
FIG. 2(b) is an SEM image of a smooth surface of a stent with a first-layer coating that has been applied by the dipping method, magnified 2,000 times.
Figure 2C:
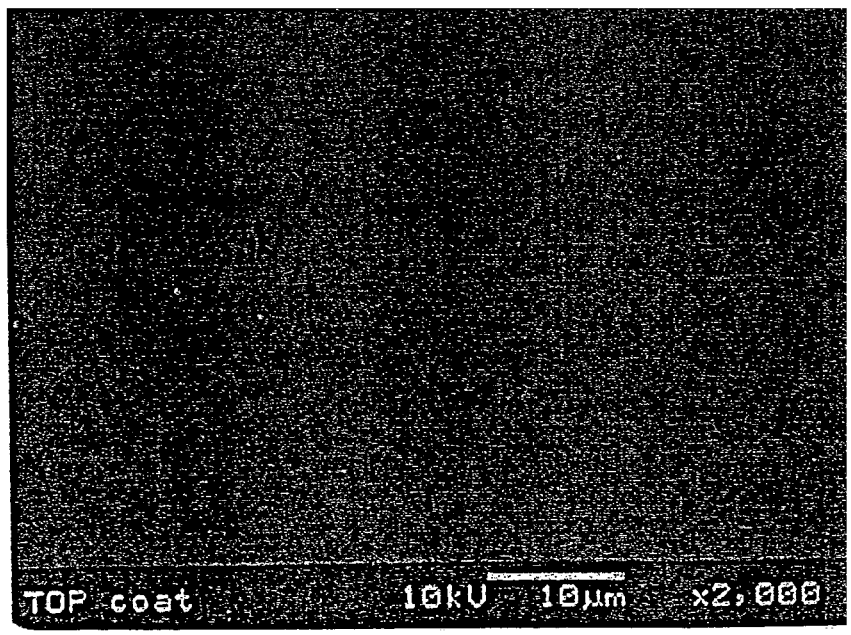
FIG. 2(c) is an SEM image of a smooth surface of a multi-layered coated stent, where both the first and second layers were applied by the dipping method, magnified 2,000 times.
Figure 3A:
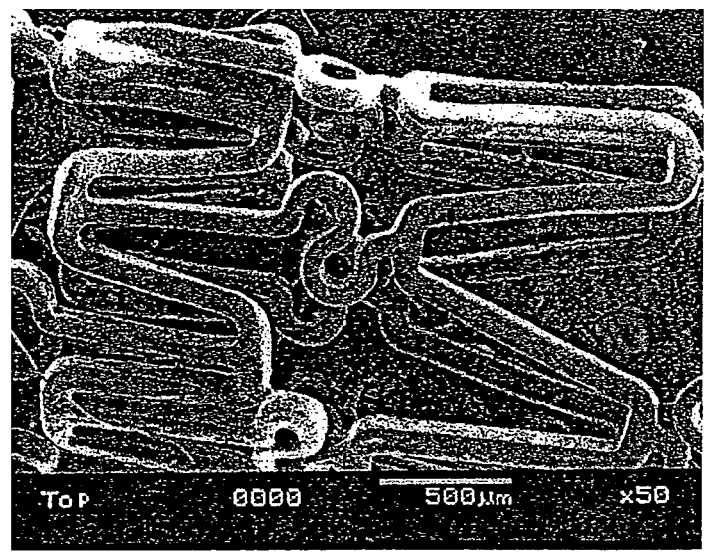
FIG. 3(a) is an SEM image of a stent surface coated by a spray-coating method, magnified 50 times.
Figure 3B:
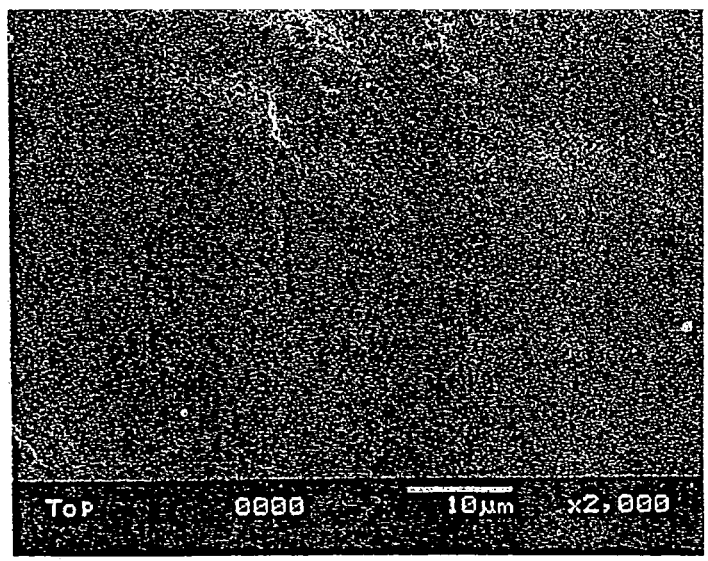
FIG. 3(b) is an SEM image of the stent surface of FIG. 3(a), magnified 2000 times.

Morphology of the Multi-Layer Coated Stent. The surface of both an uncoated and coated stent were examined under a scanning electron microscope at varying powers of magnification. The surface of the uncoated metal stent was observed to have a very rough appearance as shown in FIG. 2(a). The surface of the stent was then observed after the application of both the first layer and the second layer. In both cases, the coated surface was observed to be relatively much smoother than that of the bare stent. This held true irregardless of whether a dipping or a spaying method was used to apply the first layer. This is shown in FIGS. 2(b) and 2(c), and FIGS. 3(a) and 3(b), respectively.

EXAMPLE 5

Figure 4:
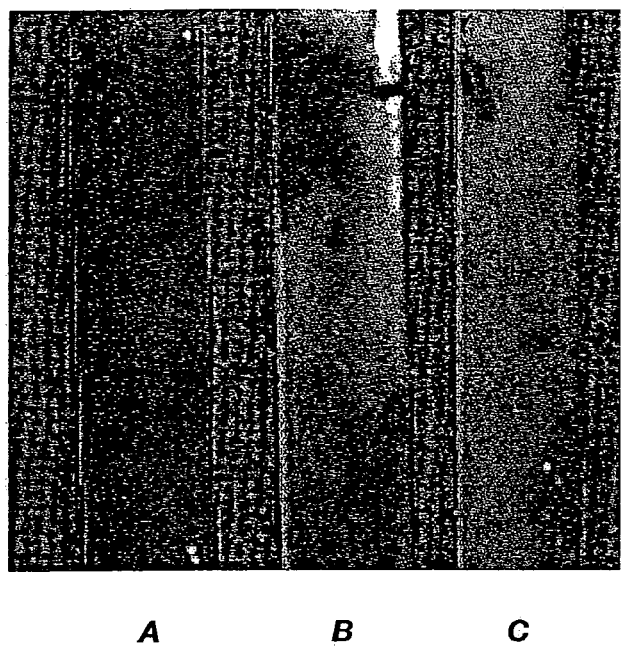
FIG. 4 shows three stent surfaces after they have undergone a whole blood test; Stent A is the bare stent, Stent B is the first-layer coated stent, and Stent C is the multi-layer coated stent.

Blood Compatibility of the Multi-Layer Coated Stent—Whole Blood Test. Three stainless steel stents, Stents A, B, and C, were provided for this test. The Stent A was left bare and had no coating applied. The Stent B had a single layer coating of polyurethane, with paclitaxel loaded therein, applied to the stent surface. Finally, the Stent C had the first-layer coating as on the second stent plus a top layer of the hydrophobic heparinized polymer. All three stents were dipped in fresh rabbit blood for a period of approximately 3 minutes. After removal, the stents were examined to determine the level of thrombus formation on the stent surfaces. The Stent A was observed to have a relatively high level of thrombus formation and blood coagulation on its surface. Stent B was observed to have a decreased amount of thrombus formation and blood coagulation, when compared to the first stent. The Stent C exhibited a reduced amount of thrombus formation when compared to the second stent. FIG. 4 shows a picture of all three stents and the varying degrees of thrombosis.

EXAMPLE 6

Figure 5A:
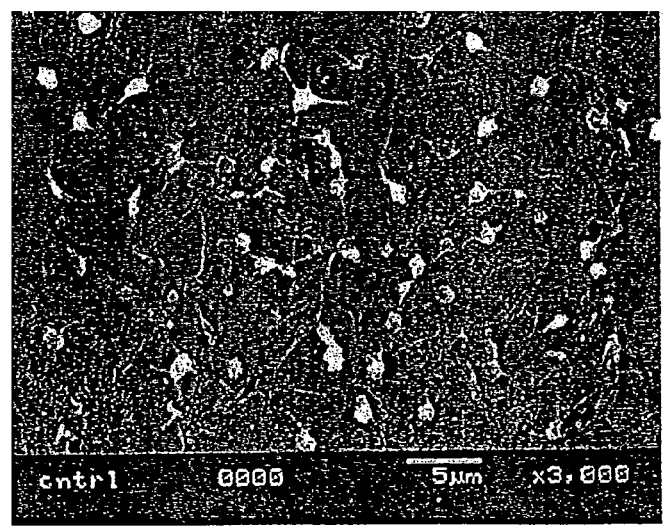
FIG. 5(a) is an SEM image of a bare stent surface after a platelet adhesion test, magnified 3000 times.
Figure 5B:
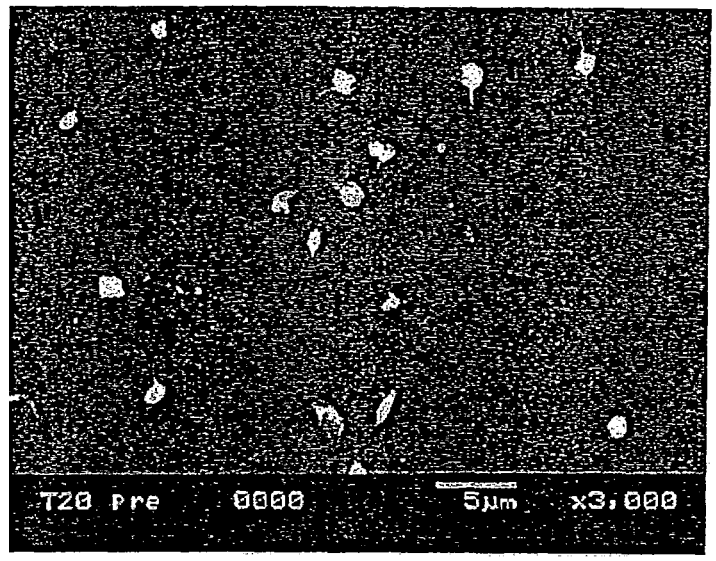
FIG. 5(b) is an SEM image of a first-layer coated stent after a platelet adhesion test, magnified 3000 times.
Figure 5C:
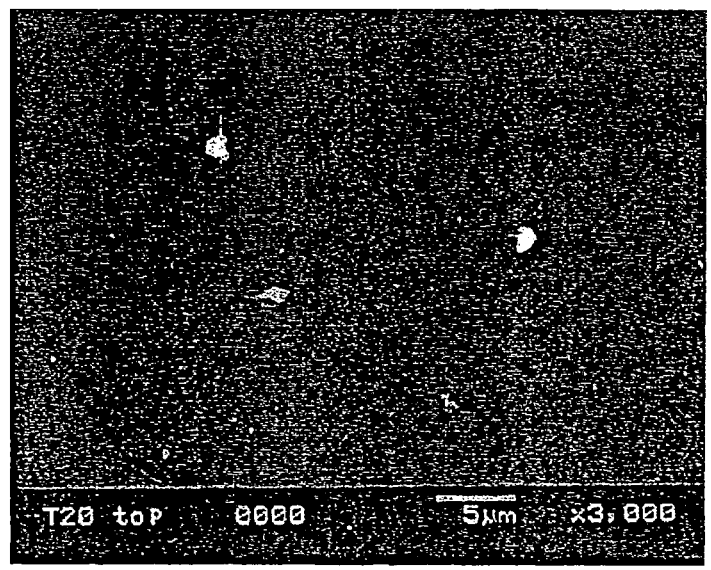
FIG. 5(c) is an SEM image of a multi-layer coated stent after a platelet adhesion test, magnified 3000 times.

Blood Compatibility of Multi-Layer Coated Stent—Platelet Adhesion Test. Fresh rabbit blood was mixed with 3.8 wt % sodium citrate solution at a 9:1 ratio concentration. The blood was then placed in a centrifuge and spun at 2,000 rpm for 10 minutes at 5° C. to isolate the platelets in a plasma. The plasma platelet concentration was manipulated by adding platelet-poor plasma, spun at 4,000 RPM, until a concentration level of $3 \times 10^5/\mu l$ was obtained. Three stainless steel stents were then prepared as in Example 5. The stents were incubated in the prepared plasma at 37° C. for approximately 1 hour. After removal, the stents were washed three times with a PBS solution. The stents then underwent a platelet fixation process which consisted of incubating the stents in 2.5% glutaraldehyde for 4 hours. Upon completion of platelet fixation, the stents were washed in 50%, 80%, and 100% ethanol aqueous solutions. After the second washing, the samples were freeze dried for 6 hours. The stents were then examined under a scanning electron microscope to determine the platelet concentration present on each of the stent's surface. The bare stent showed an uniform distribution of platelet formation on its surface as shown in FIG. 5(a). The second stent, with a single polyurethane layer, and the third stent, with the multi-layer coating, showed a decrease of 80% and 90%, respectively, in the level of platelet adhesions as shown in FIG. 5(b) and FIG. 5(c).

EXAMPLE 7

Evaluation of Inflammation of Multi-Layer Coated Stent. A number of stainless steel strips of five varying types were prepared with different compositions of surface coating. As shown in the following chart, Strip Types A, B, C, D, and E, all had either no coating, a one-layer coating, or a two-layer coating. The strips were prepared for implantation into male Sprague-Dawley rats.

| Strip Type | First Layer | Second Layer |
| --- | --- | --- |
| A | None | None |
| B | polyurethane loaded with paclitaxel (20 wt %) | None |
| C | polyurethane loaded with paclitaxel (20 wt %) | hydrophobic heparinized polymer |
| D | polyurethane loaded with paclitaxel (20 wt %) and dexamethasone (5 wt %) | None |
| E | polyurethane loaded with paclitaxel (20 wt %) and dexamethasone (5 wt %) | hydrophobic heparinized polymer |

The rats, weighing between 200-300 g, were chosen at random. The rats were first anesthetized with diethyl ether gas and secured to an operating table. One of the five types of steel strips was inserted into the back of each rat through an incision made by a scalpel. The strips were then recovered after either 14 or 30 days. The strips were recovered by anesthetizing the rats again with diethyl ether and then surgically removing a region right below where the strip had been inserted as well as the regions of tissue where it appeared that restenosis has occurred. After removal, the strip and tissue were washed with a PBS buffer solution. The tissue was then fixed with a 4% formaldehyde solution. Each strip was then visually examined to determine the level of restenosis, if any, that had developed relative to the other strips.

Figure 6A:
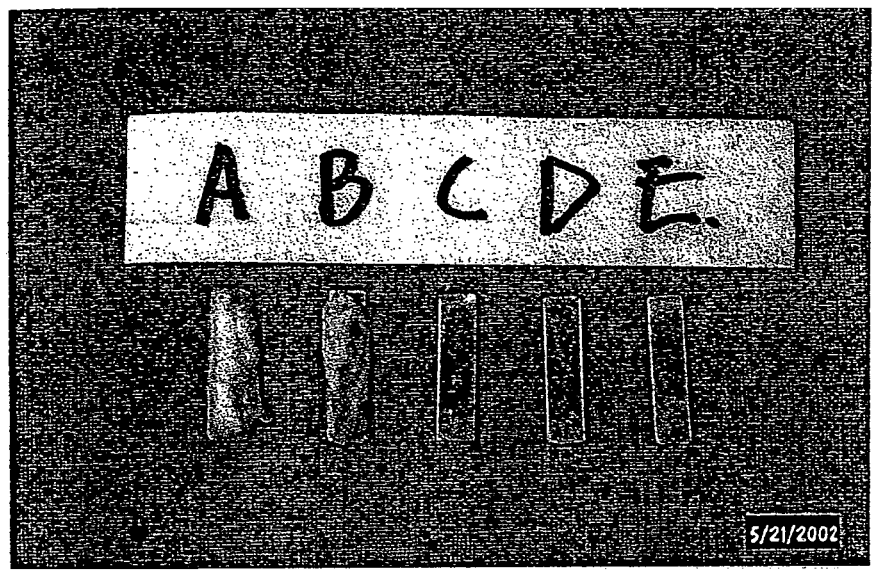
FIG. 6(a) shows five distinctly coated strips after 14 days inside of male Sprague-Dawley rats, each of the strips exhibiting different levels of inflammation.

After 14 days, the bare strip types, Strip Type A, showed severe restenosis. For those strips that had had paclitaxel loaded in polyurethane applied as primary coating, Strip Type B, a considerable degree of restenosis was observed. On the other hand, strips that had a second coating of a hydrophobic heparinized polymer, Strip Type C, had almost no restenosis. Moreover, when the specimen that had received a strip whose first layer of polyurethane had been loaded with dexamethasone, an anti-inflammatory drug, and paclitaxel, Strip Type D, those specimens showed almost no restenosis. The same held true for specimens that had an additional second layer of a hydrophobic heparinized polymer, Strip Type E. These results are shown in FIG. 6(a).

Figure 6B:
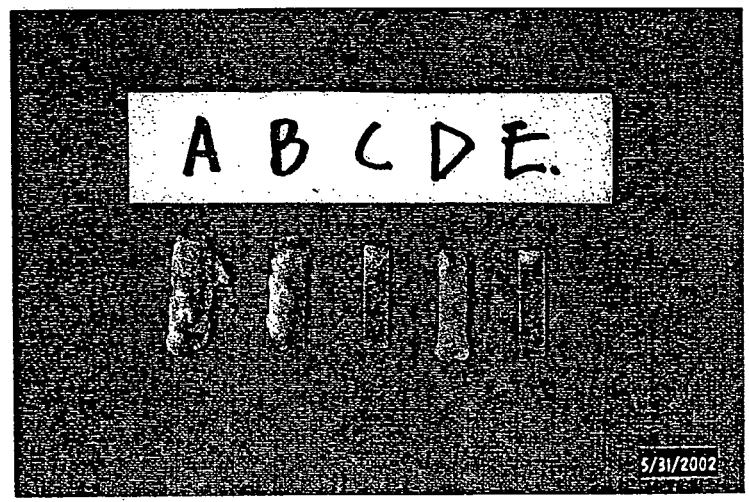
FIG. 6(b) shows five distinctly coated strips as in FIG. 6(a) after 30 days inside of male Sprague-Dawley rats, each of the strips exhibiting different levels of inflammation.

After 30 days, severe restenosis was observed on both the uncoated strips, Strip Type A, and on the single layered strips loaded with paclitaxel, Strip Type B. In strips loaded with paclitaxel and dexamethasone, Strip Type D, restenosis was also observed. However, when a hydrophobic heparinized polymer was applied as an outer layer, Strip Types C and E, no restenosis could be observed. This results are shown in FIG. 6(b).

EXAMPLE 8

Elution of Paclitaxel from the Multi-Layer Coated Film. The amount of paclitaxel eluted from a single layer polyurethane coating on a stainless steel sample was compared to a multi-layered coated sample. Both samples were incubated separately in a buffer solution at 37° C. The eluted paclitaxel was measured at 4, 8, 12, 24, 36, 48, 60, 144, 216 hours by an extraction method comprising the following steps. First, the solution was extracted by using 6 ml DCM per 100 ml buffer solution with strong agitation for about 15 seconds. Next, the solution in DCM part was separated and dried under nitrogen gas. Finally, the extracted paclitaxel was dissolved in 1 ml acetonitrile and measured by HPLC.

Figure 7A:
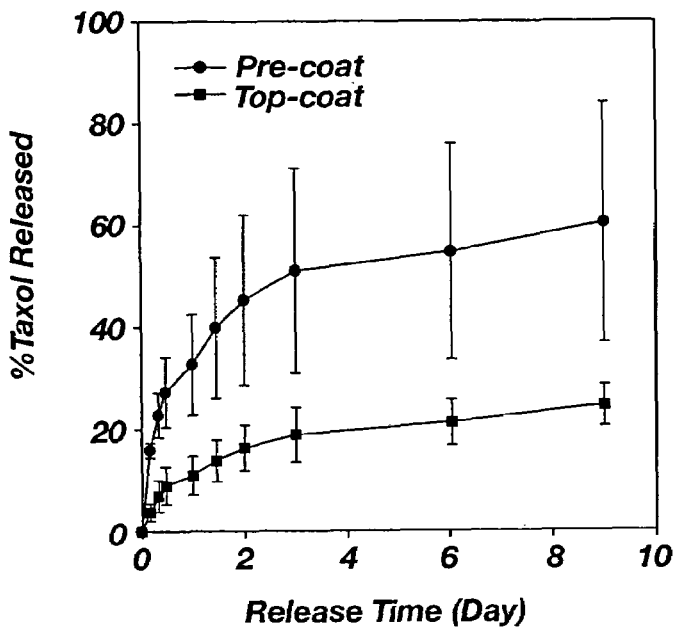
FIG. 7(a) illustrates the percentage of paclitaxel released for both a single layer coating and a multi-layer coating over a nine-day period.
Figure 7B:
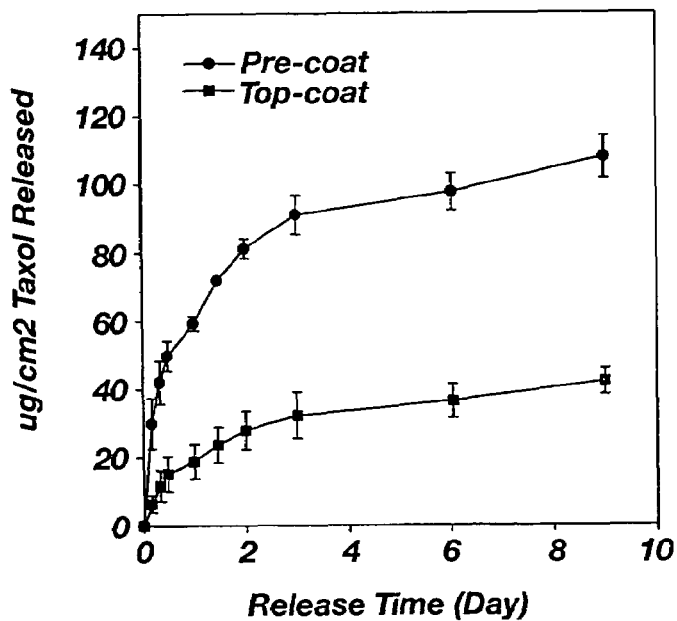
FIG. 7(b) illustrates the amount of paclitaxel released per unit area for both a single layer coating and a multi-layer coating over a nine-day period.

As shown in FIGS. 7(a) and 7(b), the elution rate of paclitaxel from the multi-layer coated film showed a decreased burst release and a more sustained release pattern, when compared to single-layer coated film.

EXAMPLE 9

Figure 8A:
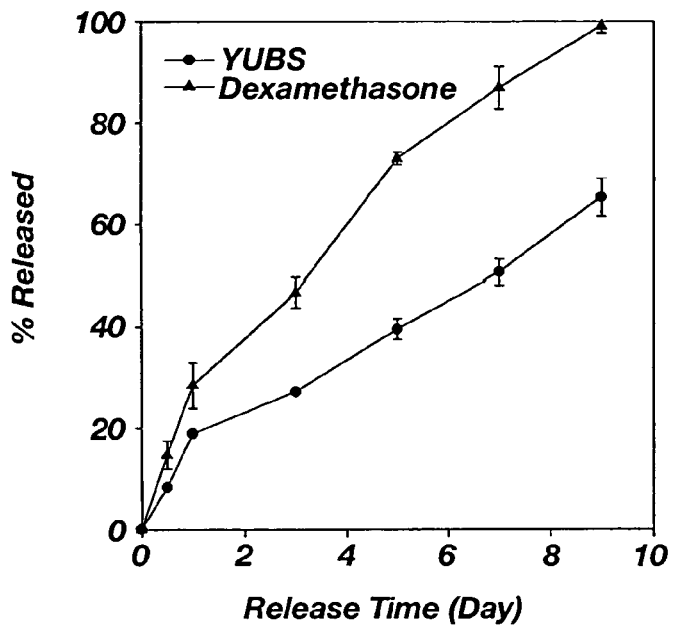
FIG. 8(a) illustrates the percentage of echinomycin and dexamethasone released over a nine day period for a multi-layered coating.
Figure 8B:
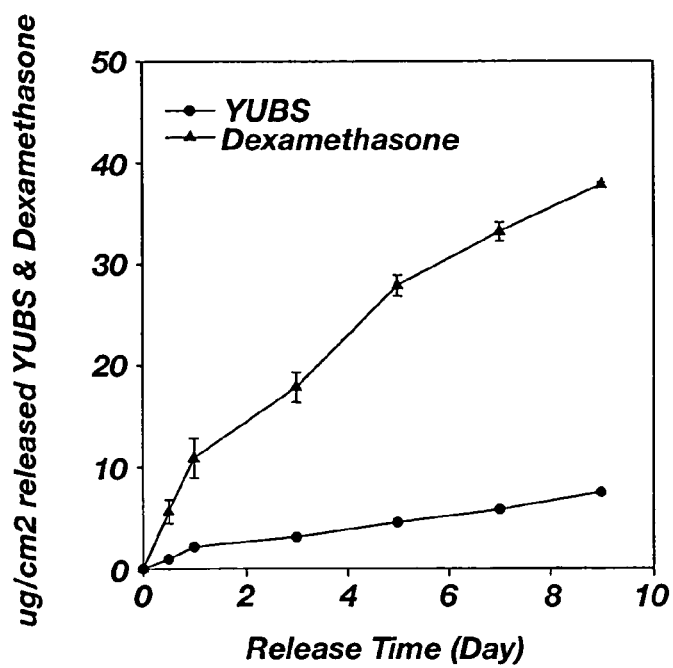
FIG. 8(b) illustrates the amount of echinomycin and dexamethasone released per unit area over a nine day period for a multi-layered coating.
Figure 9A:
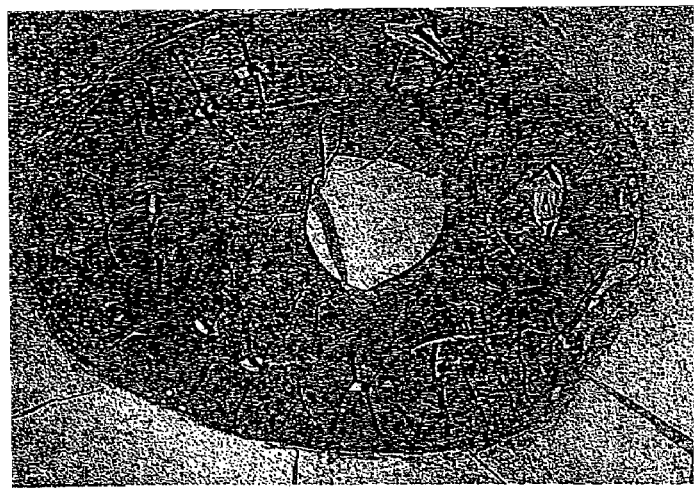
FIG. 9(a) shows a cross-section of a blood vessel in which a bare stent was implanted.
Figure 9B:
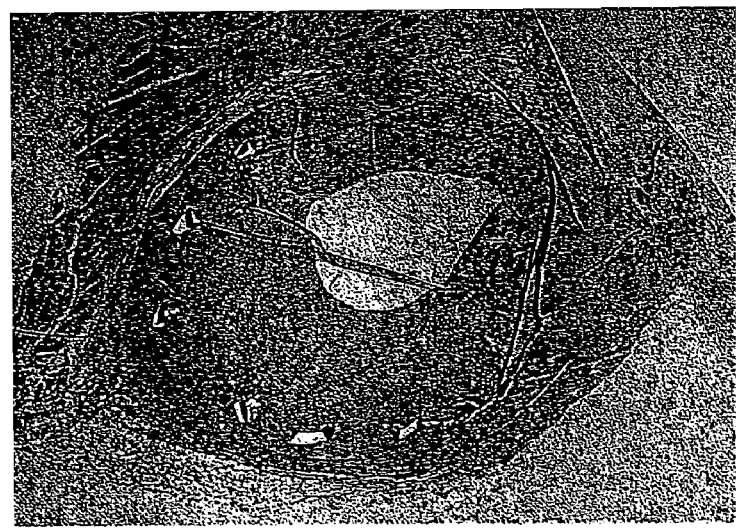
FIG. 9(b) shows a cross-section of a blood vessel in which a multi-layer coated stent was implanted with a 0.1% loading of echinomycin in the first layer.
Figure 9C:
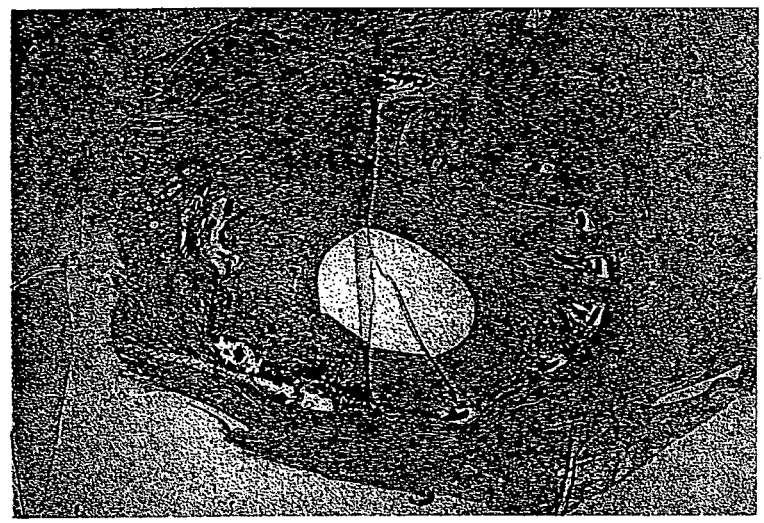
FIG. 9(c) shows a cross-section of a blood vessel in which a multi-layer coated stent was implanted with a 1% loading of echinomycin in the first layer.
Figure 9D:
FIG. 9(d) shows a cross-section of a blood vessel in which a multi-layer coated stent was implanted with a 5% loading of echinomycin in the first layer.
Figure 10:
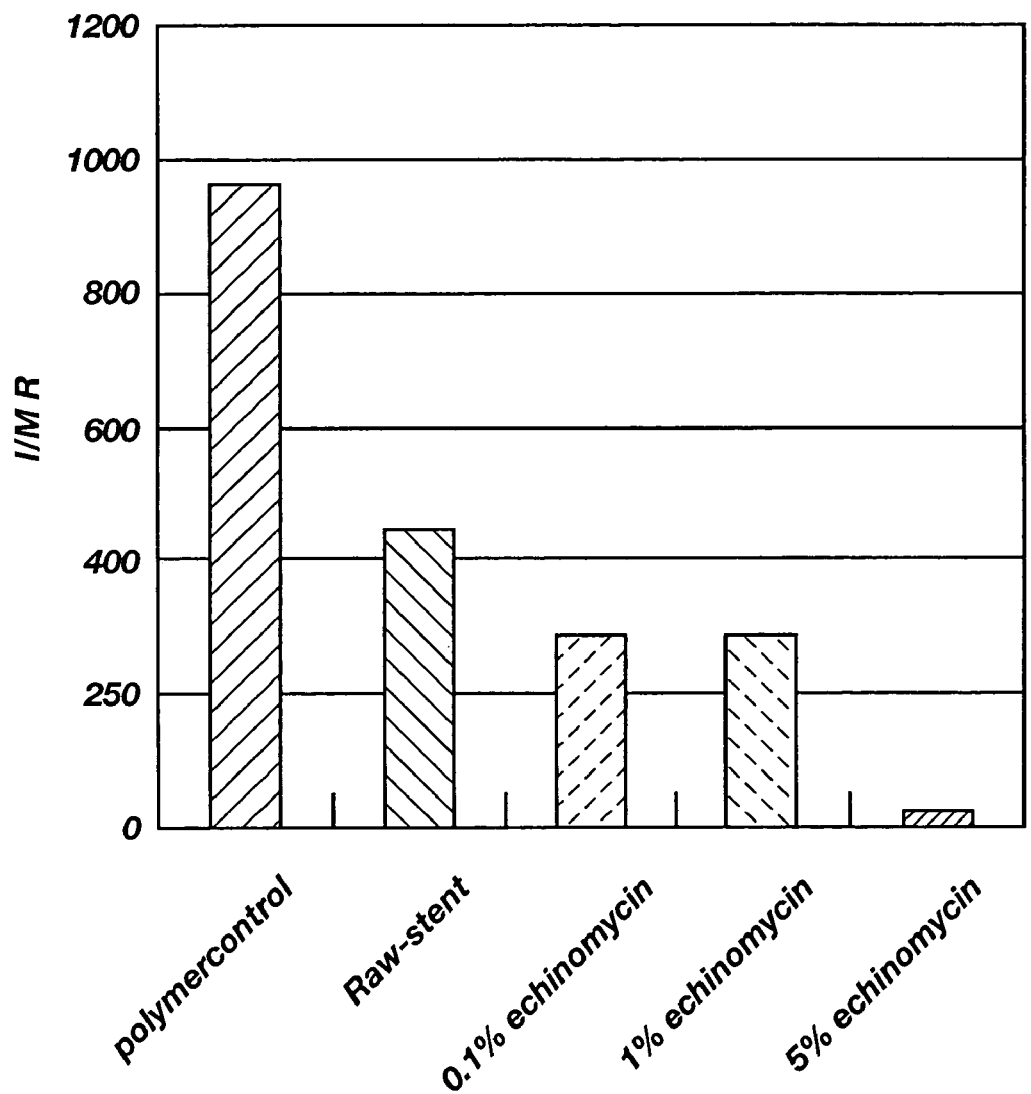
FIG. 10 illustrates a restenosis evaluation by the comparison of intima versus media (intima/media).

Elution of Echinomycin from the Multi-Layer Coated Stent. The elution of echinomycin from a multi-layered coated stent was evaluated. Multi-layer coated stents were prepared using the method of Example 2, except that echinomycin was loaded into the first layer and not paclitaxel. The loading amount of echinomycin was 3 wt %, and the spray coating process was repeated 10 times. The second layer was formed by a dip coating with 1 wt % hydrophobic heparinized polymer solution. As shown in FIGS. 8(a) and 8(b), the elution rate of paclitaxel from the multi-layer coated film showed a decreased burst release and a more sustained release pattern, when compared to single-layer coated film.

EXAMPLE 10

Elution of Dexamethasone from the Multi-Layer Coated Stent. Dexamethasone was loaded into the polyurethane first layer of a coated stent at 5 wt %. A second layer was applied by a dipping method in a 1 wt % hydrophobic heparinized polymer solution as described in Example 1. The elution rate of dexamethasone from the coated stent was then measured. As shown in FIGS. 8(a) and 8(b), the dexamethasone showed a decreased burst release, and the elution rate was higher than that of echinomycin as in Example 9.

EXAMPLE 11

Evaluation of Restenosis for Multi-Layer Coated Stent—Stent Preparation and Animal Selection. Five groups of three stents each were first prepared, the stents of each group having the same coating (or no coating), and each group having a distinct coating, varying both in the number of layers and drug composition and/or concentration. Each group had one of the following coatings: a polymer control stent, a bare stent, and three multi-layer coated stents having a hydrophobic heparinized polymer outer layer and echinomycin loaded at 0.1% wt, 1% wt or 5% wt. Fifteen pigs were then selected and divided at random into groups containing three pigs each. The average pig weighed 23 kg and prior to the experiment, the pigs were all kept in the same conditions and fed an experimental feed devoid of lipids. The pigs were also administered 300 mg/day of aspirin through their feed.

EXAMPLE 12

Evaluation of Restenosis for Multi-Layer Coated Stent—Methods of Experiment. Each pig was systemically anesthetized with an injection of ketamine (22 mg/kg) and prepared for surgery. Next, an incision was made in the front of the neck at the midline exposing the carotid artery. A dose of heparin (300 U/kg) was injected into the artery of the pig at this time. An 8 French artery guide-wire was then inserted into the carotid artery through a small incision in the arterial wall. A guide catheter was then inserted and maneuvered to, and inside of, the left and right coronary artery. An appropriate site on the right coronary artery was selected with the use of a coronary artery angiography.

The appropriate stent was attached to a balloon catheter having a balloon capable of expanding to 10-20% larger than the diameter of the coronary artery. The balloon catheter was maneuvered to the site previously selected in the coronary artery and the balloon was inflated to its maximum size for 30 seconds at 4-12 atmospheric pressure to intentionally damage the coronary artery. After the balloon was deflated, the stent remained at the site. It should be noted, that in order to block the coronary artery spasm following the blood vessel damage, nitroglycerin (200 µg) was continuously administered into the coronary artery through the guiding catheter. After the operation, a coronary artery angiography was conducted to observe the degree of damage to the coronary artery and the patency of the blood flow. The artery guide-wire was then removed and the slit in the carotid artery was ligated.

After 28 days, the pigs were again anesthetized and a guide-wire inserted as before. A dose of heparin (300 U/kg) was again injected via guide-wire into the artery. After confirming the patency of the blood vessels in the coronary artery, lethal amounts of pentothal and potassium chloride were injected via the guide catheter to induce euthanasia. The pig's heart was then removed through the thorax. The heart was then subjected to a perfusion-fixation procedure. Before sacrificing the animals, follow-up coronary angiography using OEC (GE medical, USA) was employed to determine the size of blood vessels and pictures taken before and after blood vessel damage were evaluated in order to determine the location and degree of arterial narrowing of the stented coronary segment.

EXAMPLE 13

Evaluation of Restenosis for Multi-Layer Coated Stent—Histological Evaluation. The damaged portion of the artery along with an additional 2 cm region around the damaged site was removed from the heart. The specimen containing the stent was fixed using the Embedding System (Technovit 7100, Kulzer, Germany). The specimen was then sliced into thin pieces with the use of a microtome equipped with a tungsten blade. Each slice was dyed with hematoxylin-eosin and elastic Van Gieson.

Each slice was then studied under a microscope. The slices were evaluated using the Schwartz scale. A quantitative and morphological analysis of the slices was conducted. In particular, the lumen area, internal elastic lamina area and external elastic area, intimal area, medial area, and the I/M ratio were determined. FIGS. 9(a)-9(d) and 10 show the results and the I/M ratio. The results confirmed that the multi-layered stent whose first layer had been loaded with 1 wt % echinomycin showed a significantly reduced level of neointimal tissue volume at 28 days when compared to the other stents and especially the bare stent.

The subject matter claimed is:

1. A method for preventing burst release of a biologically active agent dispersed in a thin film polymer layer on a stent comprising applying a second layer over the thin film polymer layer; said second layer being comprised of a hydrophobic heparinized polymer comprising a macromolecule, a hydrophobic material, and heparin bound together by covalent bonds, wherein the macromolecule comprises a protein selected from protamine, polylysine, polyaspartic acid, polyglutamic acid, and their derivatives and copolymers, or wherein the hydrophobic material is selected from octadecylamine, alkanoic amine, bile acids, sterols, alkanoic acids, and mixtures thereof.

2. A method for inhibiting thrombosis in a medical device having a surface in contact with an organic fluid comprising coating the surface of the medical device with an antithrombogenic heparinized polymer layer comprising a macromolecule, a hydrophobic material, and heparin bound together by covalent bonds, wherein the macromolecule comprises a protein selected from protamine, polylysine, polyaspartic acid, polyglutamic acid, and their derivatives and copolymers, or wherein the hydrophobic material is selected from octadecylamine, alkanoic amine, bile acids, sterols, alkanoic acids, and mixtures thereof.

3. The method of claim 2 further comprising applying a lowermost coating, said lowermost coating disposed under the hydrophobic heparinized polymer layer and comprising an polymer having a biologically active agent dispersed therein.

4. A method for preparing an article of manufacture comprising a stent and a coating disposed thereon, the coating comprising a first layer and a second layer, the first layer comprising a polymer film with a biologically active agent dispersed therein, and the second layer comprising an antithrombogenic heparinized polymer comprising a macromolecule, a hydrophobic material, and heparin bound together with covalent bonds, wherein the macromolecule comprises a protein selected from protamine, polylysine, polyaspartic acid, polyglutamic acid, and their derivatives and copolymers, the method comprising:
    cleaning the stent with a washing agent,
    preparing the first layer by combining the polymer and biologically active agent with a solvent, thereby forming a polymer and biologically active agent mixture and applying the mixture to the stent,
    preparing the second layer by combining the antithrombogenic heparinized polymer with a solvent and applying the second layer by immersing the stent in the antithrombogenic heparinized polymer and solvent solution and then drying the stent.

5. The method of claim 4 further comprising adding a second biologically active agent to the polymer and biologically active agent mixture.

6. The method of claim 4 wherein applying the first layer coating comprises dipping the stent into the polymer and biologically active agent mixture.

7. The method of claim 4 wherein applying the first layer coating comprises spraying the polymer and biologically active agent mixture onto the stent.

8. The method of claim 4 wherein the polymer film is selected from polyurethanes, polyethylene terephthalate, PLLA-poly-glycolic acid (PGA) copolymer (PLGA), polycaprolactone, poly-(hydroxybutyrate/hydroxyvalerate) copolymer, poly(vinylpyrrolidone), polytetrafluoroethylene, poly(2-hydroxyethylmethacrylate) , poly(etherurethane urea), silicones, acrylics, epoxides, polyesters, urethanes, parlenes, polyphosphazene polymers, fluoropolymers, polyamides, polyolefins, and mixtures thereof.

9. The method of claim 4 wherein the biologically active agent dispersed in the first layer is selected from antithrombotics, anticoagulants, antiplatelet agents, thrombolytics, antiproliferatives, anticancer drugs, antiinflammatory drugs, agents that inhibit restenosis, smooth muscle cell inhibitors, antibiotics, and mixtures thereof.

10. The method of claim 4 wherein the heparin is selected from recombinant heparin, heparin derivatives, and heparin analogues.

11. A method for preparing an article of manufacture comprising a stent and a coating disposed thereon, the coating comprising a first layer and a second layer, the first layer comprising a polymer film with a biologically active agent dispersed therein, and the second layer comprising an antithrombogenic heparinized polymer comprising a macromolecule, a hydrophobic material, and heparin bound together with covalent bonds, wherein the macromolecule comprises a biopolymer selected from gelatin, collagen, alginate, hyaluronic acid, alginic acid, carrageenan, chondroitin, pectin, chitosan, and their derivatives and copolymers, the method comprising:
    cleaning the stent with a washing agent,
    preparing the first layer by combining the polymer and biologically active agent with a solvent, thereby forming a polymer and biologically active agent mixture and applying the mixture to the stent,
    preparing the second layer by combining the antithrombogenic heparinized polymer with a solvent and applying the second layer by immersing the stent in the antithrombogenic heparinized polymer and solvent solution and then drying the stent.

12. A method for preparing an article of manufacture comprising a stent and a coating disposed thereon, the coating comprising a first layer and a second layer, the first layer comprising a polymer film with a biologically active agent dispersed therein, and the second layer comprising an antithrombogenic heparinized polymer comprising a macromolecule, a hydrophobic material, and heparin bound together with covalent bonds, wherein the hydrophobic material is selected from octadecylamine, alkanoic amine, bile acids, sterols, alkanoic acids, and mixtures thereof, the method comprising:
    cleaning the stent with a washing agent,
    preparing the first layer by combining the polymer and biologically active agent with a solvent, thereby forming a polymer and biologically active agent mixture and applying the mixture to the stent,
    preparing the second layer by combining the antithrombogenic heparinized polymer with a solvent and applying the second layer by immersing the stent in the antithrombogenic heparinized polymer and solvent solution and then drying the stent.

13. The method of claim 12 further comprising adding a second biologically active agent to the polymer and biologically active agent mixture.

14. The method of claim 12 wherein applying the first layer coating comprises dipping the stent into the polymer and biologically active agent mixture.

15. The method of claim 12 wherein applying the first layer coating comprises spraying the polymer and biologically active agent mixture onto the stent.

16. The method of claim 12 wherein the polymer film is selected from polyurethanes, polyethylene terephthalate, PLLA-poly-glycolic acid (PGA) copolymer (PLGA), poly-caprolactone, poly-(hydroxybutyrate/hydroxyvalerate) copolymer, poly(vinylpyrrolidone), polytetrafluoroethylene, poly(2-hydroxyethylmethacrylate), poly(etherurethane urea), silicones, acrylics, epoxides, polyesters, urethanes, parlenes, polyphosphazene polymers, fluoropolymers, polyamides, polyolefins, and mixtures thereof.

17. The method of claim 12 wherein the biologically active agent dispersed in the first layer is selected from antithrombotics, anticoagulants, antiplatelet agents, thrombolytics, antiproliferatives, anticancer drugs, antiinflammatory drugs, agents that inhibit restenosis, smooth muscle cell inhibitors, antibiotics, and mixtures thereof.

18. The method of claim 12 wherein the macromolecule comprises a protein selected from protamine, polylysine, polyaspartic acid, polyglutamic acid, and their derivatives and copolymers.

19. The method of claim 12 wherein the heparin is selected from recombinant heparin, heparin derivatives, and heparin analogues.

\* \* \* \* \*